(12) United States Patent
Asemyr

(10) Patent No.: US 6,768,544 B1
(45) Date of Patent: Jul. 27, 2004

(54) METHOD AND A SYSTEM FOR DETECTING IMPURITIES IN A TRANSPARENT MATERIAL

(75) Inventor: Göran Asemyr, Onsala (SE)

(73) Assignee: Semyre Photonic Systems AB, Stenungsund (SE)

( * ) Notice: Subject to any disclaimer, the term of this patent is extended or adjusted under 35 U.S.C. 154(b) by 0 days.

(21) Appl. No.: 09/958,636

(22) PCT Filed: Apr. 10, 2000

(86) PCT No.: PCT/SE00/00681

§ 371 (c)(1),
(2), (4) Date: Oct. 12, 2001

(87) PCT Pub. No.: WO00/62045

PCT Pub. Date: Oct. 19, 2000

(30) Foreign Application Priority Data

Apr. 12, 1999 (SE) .............................................. 9901291

(51) Int. Cl.⁷ .............................................. G01N 21/89
(52) U.S. Cl. .................................. 356/239.1; 250/559.2
(58) Field of Search ...................... 356/239.1, 432–435, 356/429, 430; 250/559.2, 559.39, 559.46

(56) References Cited

U.S. PATENT DOCUMENTS

| | | | |
|---|---|---|---|
| 4,442,054 A | | 4/1984 | Dane et al. |
| 4,756,855 A | | 7/1988 | Mathis et al. |
| 4,973,437 A | | 11/1990 | Yanagisawa |
| 5,220,178 A | * | 6/1993 | Dreiling et al. ........ 250/559.03 |
| 5,243,402 A | * | 9/1993 | Weber et al. ............... 356/429 |
| 5,452,079 A | * | 9/1995 | Okugawa ................. 356/239.1 |
| 6,011,620 A | * | 1/2000 | Sites et al. ............... 356/239.1 |
| 2002/0154307 A1 | * | 10/2002 | Bjork ......................... 356/430 |

FOREIGN PATENT DOCUMENTS

WO     WO 97/43624     11/1997

* cited by examiner

Primary Examiner—Richard A. Rosenberger
Assistant Examiner—Vincent P. Barth
(74) Attorney, Agent, or Firm—Nixon & Vanderhye P.C.

(57) ABSTRACT

In a method for detecting impurities in a transparent material, the material (2) is scanned line by line and the light transmission through the material is measured and compared with a reference value. If the transmission value at one point of the material is in a predetermined relation to said reference value, indicating the occurrence of impurities, the light transmission is studied in an area around the measured point for this transmission value in order to determine the extent and shape of the impurity, the light transmission values in the central area of the impurity being compared with transmission values measured in surrounding parts of the impurity to determine whether the impurity is of gel type or an impurity of some other type. A system for detecting impurities in a transparent material, which system comprises a camera (6) arranged to scan the material (2) and register light transmitted through the material in the form of pixel values, and a first comparator (8) for comparing said pixel values with a reference value. If a pixel value is in a predetermined relation to said reference value, a signal processor (12) analyses registered pixel values from an area of the material around said pixel value in order to determine a centre for the impurity and compare pixel values in said centre with pixel values in the surrounding parts of the impurity to determine whether the impurity is an impurity of gel type or an impurity of some other type.

14 Claims, 2 Drawing Sheets

No 1

No 2

No 3

No 4

No 5

No 6

No 7

No 8

No 9

No 10

METHOD AND A SYSTEM FOR DETECTING IMPURITIES IN A TRANSPARENT MATERIAL

Figure 1:
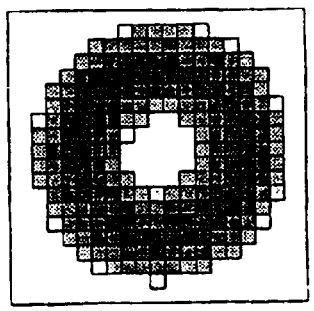
Figure 1:
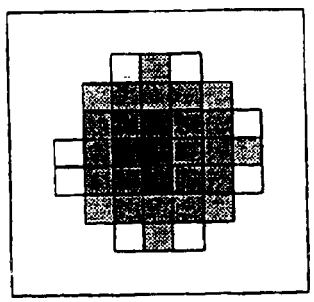
Figure 1:
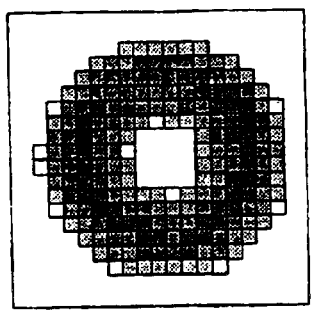
Figure 1:
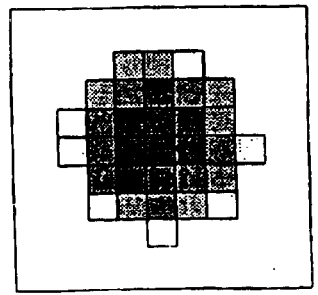
Figure 1:
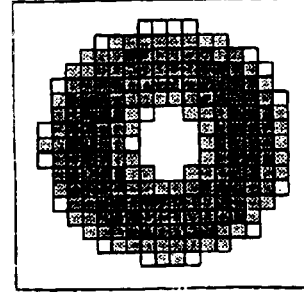
Figure 1:
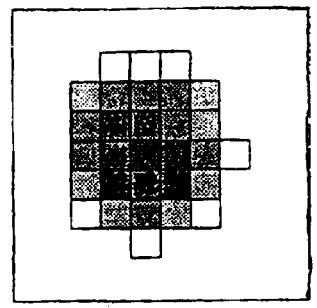
Figure 1:
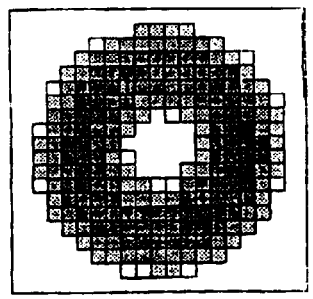
Figure 1:
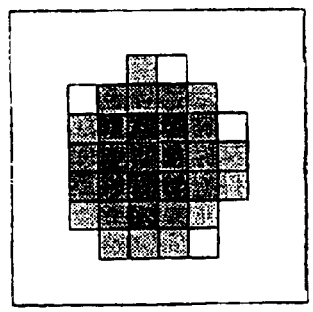
Figure 1:
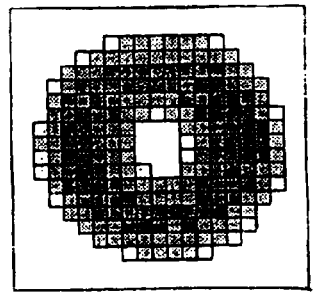
Figure 1:
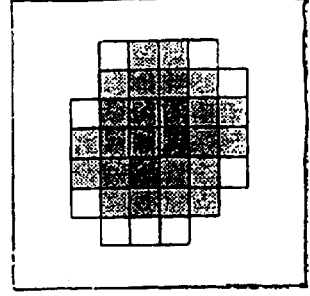

The present invention relates to a method for detecting impurities in transparent material whereby the material is scanned line by line and the light transmission through the material is measured and compared with a reference value, and also to a system for detecting impurities in a transparent material, which system comprises a camera arranged to scan the material and register light transmitted through the material in the form of pixel values, and a first comparator for comparing said pixel values with a reference value.

The present invention relates primarily to detecting various types of impurities in transparent polyethylene or polypropylene materials for various uses, such as the production of pipes, cable casing, thin films, etc.

The starting material used in the production of such polyethylene or polypropylene materials is in the form of pellets which are heated to a molten mass and compressed to form a tape or film. During this procedure clumps of molecules may be formed having a different structure from the surrounding material. The reason for these clumps of molecules, named gels in this context, may be poor melting of the starting material or deficiencies in earlier polymerisation steps for producing the starting material. The gels thus constitute a kind of lack of homogeneity in the material produced, in the form of collections or clumps of molecules with a different, incorrect structure from the surrounding flawless material. These gels are at least as hard as the surrounding material and may even be harder. The accepted definition of a gel as something that has coagulated to an elastic, semi-solid mass thus does not coincide with the clumps of molecules that are termed gels in the present context.

Gels have special optical properties. They function as lenses, and this property is utilized in the technology known hitherto for gel detection. The optical properties of the gel thus deviate from those of the surrounding material and gels have hitherto been detected using equipment comprising a light source and a light detector, the optical axes of which are displaced so that the detector does not normally see the point illuminated by the light source and only does so when something changes the light deflection, i.e. a gel appears so that the light is deflected into the detector, see U.S. Pat. No. 4,492,477 and WO 97/43624, for instance. The drawback of this previously known technology is that it does not permit simultaneous detection and separation of gels and other types of impurities.

Gels may be of extremely varying sizes and have different shapes, usually annular even if only a circle segment is detectable. Common to the gels, however, is that they have a lighter central part, i.e. a central part with higher light transparency than surrounding parts, as compared with other types of impurities that are usually darkest at or in the vicinity of the centre. This difference in transparency between the various types of impurities is utilised in the present invention in order to alleviate the drawbacks with the previously known technology.

The object of the present invention is thus to provide a method and a system for detecting different types of impurities in a transparent material and to separate the impurities.

This object is achieved with a method and a system of the type described in the introduction, with the characterizing features defined in claims 1 and 6, respectively.

The present invention is thus based on pattern recognition. As mentioned above, gels and other types of impurities produce different light transmission patterns upon illumination and according to the invention pattern recognition technology is utilised not only to detect different types of impurities but also to separate them. According to the present invention, thus, "areas of interest" are detected first by comparing the light transmission with a reference value, whereupon this area is then analysed in more detail in order to determine the impurity. In this way a great majority, up to 99%, of the light transmission data can be sorted out since areas of interest appear rather seldom. This reduction or compression of data facilitates the subsequent analysis of light transmission values measured so that, even if the light transmission data from such "areas of interest" arrive in showers, these showers of data can be processed in the following in a relatively simple manner.

According to advantageous embodiments of the method according to the invention light transmission values measured are compared with the reference value of the light transmission in order to determine the extent and shape of the impurity. The centre of the impurity is determined on the basis of its extent and shape. Higher light transmissions measured in the centre of the impurity than in the surrounding parts are indicated as an impurity of gel type. As mentioned, the gels are often circular even if only a circle segment is detectable.

According to an advantageous embodiment of the system according to the invention, a reference-producing unit is arranged to produce the reference value from the value or values of one or more selected pixels measured previously. By utilising a floating reference value in this way instead of a fixed reference value as in previously known technology, the sensitivity of the system is increased for detecting small changes in the material being scanned, and by also choosing a value from a greater or smaller number of previously measured pixel values as reference value, the sensitivity of the detection can be controlled.

According to another advantageous embodiment of the system according to the invention, the reference-producing unit is arranged to produce a reference value from the mean value of the values of a predetermined number of pixels immediately prior to the pixel being currently scanned. The relevant pixel is thus compared with a reference deriving from recent previous pixel values, which makes this embodiment suitable for detecting rapid changes in the material being monitored or scanned.

According to other advantageous embodiments of the system according to the invention, wherein the camera is a linear camera for scanning the material line by line, scanned lines are stored line by line and the reference-producing unit is arranged to choose as reference value the value of the pixel in a selected stored line corresponding to the relevant pixel in the line being scanned. These stored reference lines provide a sort of historical record containing information as to how the appearance of the scanned material has varied previously. In this embodiment of the system according to the invention, changes in the scanned material are determined over a period of time that can be chosen through the choice of reference line. By choosing a "recently" stored reference line immediately before the new, incoming line, the change is measured over a short time interval. This is advantageous if rapid changes are to be detected. To detect slower changes, the line being scanned is compared with a reference line stored longer ago, i.e. a comparison in time is made over shorter or longer periods depending on the requirement of the measurement in progress. By choosing the time over which changes shall be detected, thus, the sensitivity of detection can be adapted to current requirements. The time shift between the stored lines in turn corresponds to a certain spatial displacement in the case of movable material.

Figure 2:
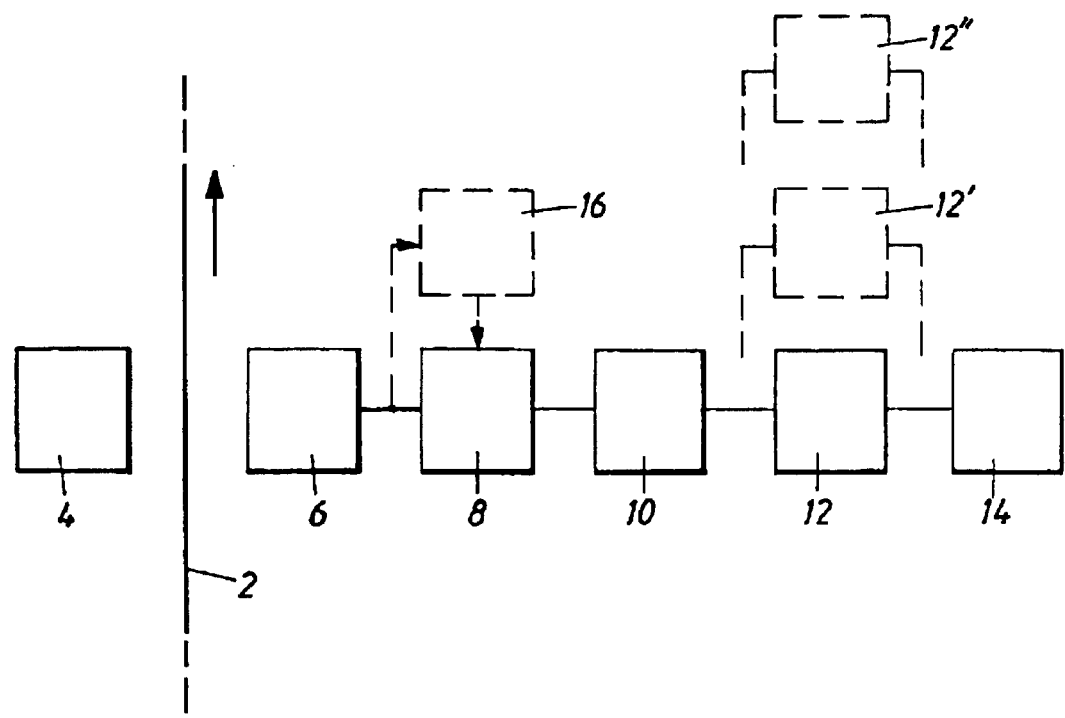

To explain the invention in more detail one embodiment of the system according to the invention will be described by way of example, with reference to the accompanying drawings in which FIG. 1 illustrates measurements of gels and other impurities using the system according to the invention, and FIG. 2 shows a block diagram of an embodiment of the system according to the invention as an example.

FIG. 1 shows various examples of impurities detected using the system according to the invention. As can be seen, some of the impurities are of gel type, see measurements Nos. 1, 3, 5, 7 and 9, as can be seen from their substantially circular shape and lighter central parts than the surrounding area, and some are "ordinary" impurities of various types, see measurements Nos. 2, 4, 6, 8 and 10, as can be seen since they are darkest in or close to the centre, i.e. the light transmission is lowest there.

An example of the system according to the invention is illustrated in block diagram form in FIG. 2. An extruded polyethylene or polypropylene material 2 is caused to pass between a light source 4 and a detector 6. A CCD linear camera is used as detector. The camera 6 emits the light transmission data for each individual scanned pixel with high, constant pixel frequency, which does not allow for direct data processing in a conventional computer. The data speed is therefore geared down by first determining "areas of interest" in the material 2. This is performed by hardware in a first comparator 8. In this comparator 8 pixel values measured are compared with a reference value. A light transmission value is selected as reference value, which is lower than the basic value corresponding to the light transmission in the case of clear material.

"Areas of interest" are thus selected by means of this procedure, performed at full pixel speed, and are stored in a buffer memory 10. These stored data constitute only a small part of the total flow of information from the camera 6. Thus often up to 99% of all pixel data can be sorted out since "areas of interest" usually occur only seldom. Even if pixel data from such "areas of interest" arrive in showers, these showers of data can be processed in subsequent processing apparatus since the showers are relatively few and far between.

In the present invention, thus, two trigger levels are used: one level for determining "areas of interest" which result in the number of detected impurities, and a second level that normally responds to higher light transmission than the first mentioned level and indicates the size and shape of the impurity.

Determination of "areas of interest" in the first comparator 8 is usually effected by comparison with a fixed reference value. Alternatively, however, a reference-forming unit 16 may be arranged to produce the reference value in some other way such as from the value or values of one or more selected pixels measured previously. Alternatively the reference value may be calculated as the mean value of the values of a predetermined number of pixels immediately before the relevant pixel currently being scanned, or the reference-forming unit 16 can be arranged to choose the value of the pixel in a selected line corresponding to the relevant pixel in the line being scanned, as reference value, or the reference-forming unit 16 may be arranged to form the reference value from the mean value of the pixels corresponding to the relevant pixel in the line being scanned in a predetermined number of selected lines of said stored lines.

The buffer memory 10 is read by a digital signal processor 12 which is a rapid processor that normally manages the required calculations at the speed thus reduced. Several such processors 12, 12', 12" may possibly be arranged in parallel if necessary.

The signal processor 12 comprises a second comparator to compare the pixel values supplied, with a base value representing the light transmission through the material, in order to determine the shape and extent of the impurity, in order to separate and determine the size of gels and other types of impurities from transmission levels analysed in this way. The result of this analysis is then transferred to a system computer 14 for compiling and reporting for classification of the scanned material 2, for instance.

The camera is suitably a linear camera of commercially available standard type, designed typically for 1024–8192 pixels per line, which is read continuously with constant frequency. Other units in the system are suitably realised by means of image-processing PC boards.

Thus when a spot appears on the transparent material 2 which decreases the light transmission sufficiently, signals are emitted from a number of scanning lines before the trigger point, from all lines as long as the light transmission lies below the reference value, and from a number of scanning lines after the transmission level has again exceeded the reference value, to the buffer member 10 and the signal processor 12. The signal analysis then reveals if this is a question of an impurity of gel type or some other type of impurity, or if several impurities are present. An impurity generally extends over only a few pixels, see FIG. 1, whereas the entire surface or area is analysed in the signal processor 12. This enables other defects, not detected in the comparator 8, to be detected. The signal processor 12 may also be programmed to include rules for whether the impurities shall be classed as coherent or not, depending on how many intermediate pixels exist with the base line level of light transmission.

As can be seen from FIG. 1, the light central part of impurities of gel type often constitutes an area of the size of a few pixels.

The conditions for a detected impurity to be classed as an impurity of gel type are thus 1) at least one pixel exists with a light transmission value that is above or equal to the basic value used for comparison in the signal processor and this pixel is surrounded by pixels having a light transmission level below the basic value utilised in the signal processor and/or below the reference value used in the comparator 8, or
2) at least one pixel exists having a light transmission value above the basic value utilised in the signal processor 12, that is surrounded by pixels having a light transmission below the reference value in the comparator 8.

It may also be prescribed that the light, central area shall comprise several coherent pixels, e.g. 4 or 5 coherent pixels, surrounded by darker areas, before the impurity is classified as a gel.

What is claimed is:

1. A method for detecting impurities in transparent material wherein the material is scanned line-by-line and the light transmission through the material is measured, said method comprising the steps of:
   (a) comparing the measured light transmission values and a reference value to indicate the occurrence of an impurity in the transparent material at one location thereof;

(b) determining the extent and shape of the located impurity; and (c) comparing light transmission values in the central area of the located impurity with light transmission values measured in parts of said located impurity surrounding the located impurity said central area of the impurity to determine whether the impurity is a gel or an impurity of some type other than a gel, wherein said gel is an impurity in the transparent material having a central part with greater light transparency than surrounding parts and said impurity of a type other than a gel is an impurity in the transparent material having a central part with lesser light transparency than surrounding parts.

2. A method according to claim 1 including using, in step (a), a light transmission value lower than a basic value of light transmission through an area of the transparent material without impurities as said reference value.

3. A method according to claim 1 wherein step (b) includes comparing said light transmission values measured in the central area of the located impurity and a basic value of light transmission through areas of the transparent material without impurities.

4. A method according to claim 1 including determining the center of the impurity on the basis of the extent and shape of the impurity.

5. A method according to claim 4 including identifying the impurity as a gel in response to measuring a higher light transmission at the central area of the impurity than in surrounding parts of the impurity.

6. A system for detecting impurities in a transparent material, comprising:

a camera arranged to scan the material and register light transmitted through the material in the form of pixel values;

a first comparator for comparing said pixel values with a reference value;

a signal processor for analyzing registered pixel values from an area of the material around a pixel value, identified in a predetermined relation to said reference value, to determine a center for the impurity and to compare pixel values in said center with pixel values in the surrounding parts of the impurity to determine whether the impurity is an impurity of a gel or an impurity of a type other than a gel, wherein said gel is an impurity in the transparent material having a central part with greater light transparency than surrounding parts and said impurity of a type other than a gel is an impurity in the transparent material having a central part with lesser light transparency than surrounding parts.

7. A system according to claim 6 wherein the signal processor comprises a second comparator for comparing pixel values supplied to the signal processor with a basic value of light transmission through the material free from impurities in order to determine the shape and extent of the impurity.

8. A system according to claim 7 including a buffer memory for storing the pixel values for subsequent reading and transfer to said signal processor.

9. A system according to claim 6 including a plurality of signal processors arranged in parallel.

10. A system according to claim 6 wherein said camera is a linear camera movable in relation to the material and design for 1024–8192 pixels per line.

11. A system according to claim 6 including a reference-producing unit for producing the reference value from the value or values of one or more selected pixels measured previously.

12. A system according to claim 11 wherein the reference-producing unit is arranged to produce a reference value from the mean value of the values of a predetermined number of pixels immediately prior to the pixel being currently scanned.

13. A system according to claim 11 wherein the reference-producing unit is arranged to choose as a reference value the value of the pixel in a selected stored line corresponding to a relevant pixel in the line being scanned.

14. A system according to claim 13 wherein the reference-producing unit is arranged to produce a reference value the mean value of the pixels corresponding to the pixel in the line being scanned in a preceding number of selected lines of said lines.

* * * * *